US007384391B2

(12) United States Patent  (10) Patent No.: US 7,384,391 B2
Spittle et al.  (45) Date of Patent: Jun. 10, 2008

(54) HEATED OVUM PICK UP NEEDLE

(75) Inventors: Jason William Spittle, Queensland (AU); Michael Carl Junger, Queensland (AU); David Sean O'Brien, Queensland (AU)

(73) Assignees: William A. Cook Australia Pty. Ltd., Queensland (AU); Cook Urological Incorporated, Spencer, IN (US)

( * ) Notice: Subject to any disclaimer, the term of this patent is extended or adjusted under 35 U.S.C. 154(b) by 425 days.

(21) Appl. No.: 11/003,161

(22) Filed: Dec. 3, 2004

(65) Prior Publication Data

US 2005/0143619 A1  Jun. 30, 2005

Related U.S. Application Data

(60) Provisional application No. 60/527,250, filed on Dec. 5, 2003.

(51) Int. Cl.
*A61B 17/43* (2006.01)
*A61D 7/00* (2006.01)

(52) U.S. Cl. ........................................................ 600/33

(58) Field of Classification Search ............ 600/33–35, 600/437, 439; 604/6.13, 43, 113–114, 540, 604/523, 171; 606/20–23

See application file for complete search history.

(56) References Cited

U.S. PATENT DOCUMENTS

| 3,698,394 | A | * | 10/1972 | Piper et al. | .................... 606/29 |
| 5,063,994 | A | * | 11/1991 | Verkaart | ..................... 165/154 |
| 5,437,673 | A | * | 8/1995 | Baust et al. | ................... 606/23 |
| 6,149,673 | A | * | 11/2000 | Ginsburg | ..................... 607/96 |
| 6,726,654 | B2 | * | 4/2004 | Rosenman | ................... 604/113 |
| 6,875,168 | B2 | * | 4/2005 | Bateman et al. | .............. 600/34 |
| 2001/0017060 | A1 | * | 8/2001 | Offen et al. | .............. 73/863.11 |
| 2002/0111584 | A1 | * | 8/2002 | Walker et al. | ............... 604/113 |

* cited by examiner

*Primary Examiner*—John P Lacyk
(74) *Attorney, Agent, or Firm*—James B. Hunt

(57) ABSTRACT

An ovum collection device (20) includes a handle (4) and a collection needle (3) extending from the handle. The collection needle has a sharpened tip (44) for insertion into a follicle of an ovary. A collection duct (5) in fluid communication with the collection needle extends from the handle to a collection bottle (6). A heating arrangement (14) is used to maintain the collection needle at a selected temperature to prevent damage to an oocyte. The heating arrangement may be associated with a needle guide (72) on an ultrasonic probe such as a transvaginal ultrasonic probe (70).

8 Claims, 3 Drawing Sheets

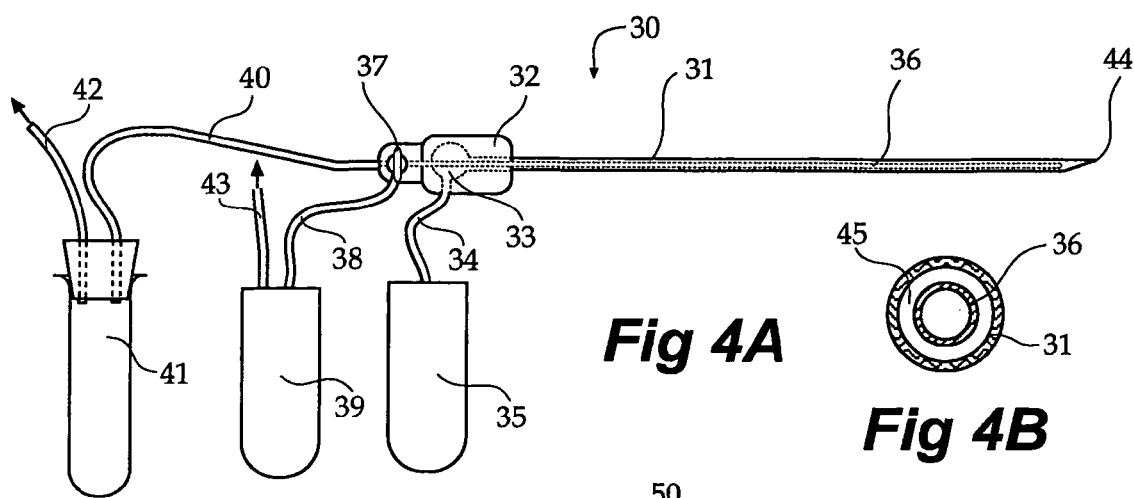
*Fig 4A*
*Fig 4B*
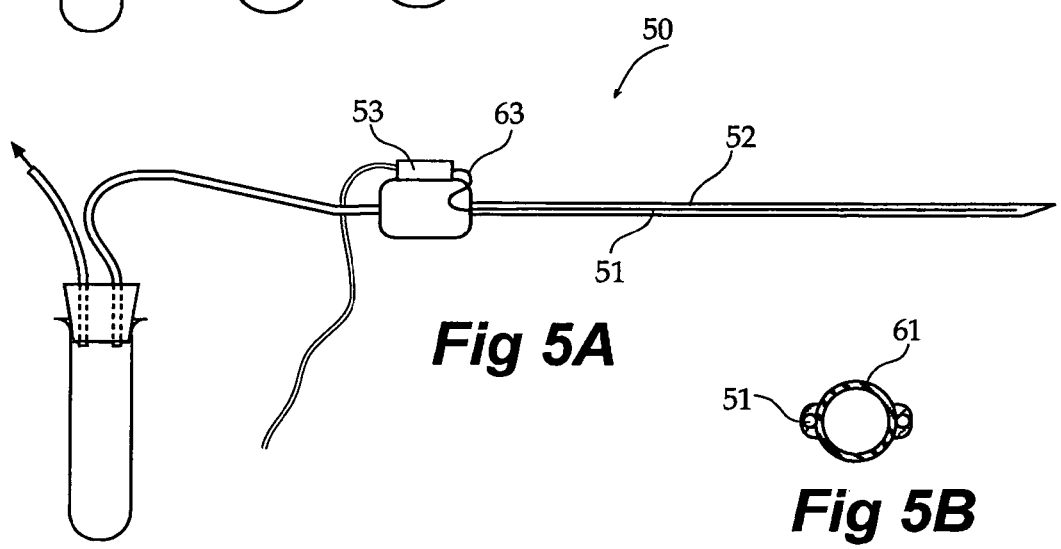
*Fig 5A*
*Fig 5B*
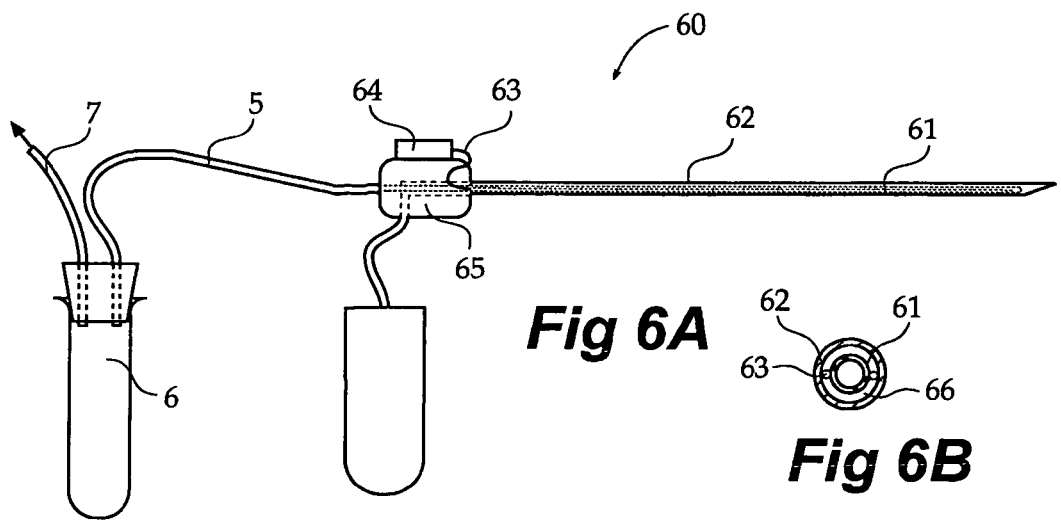
*Fig 6A*
*Fig 6B*

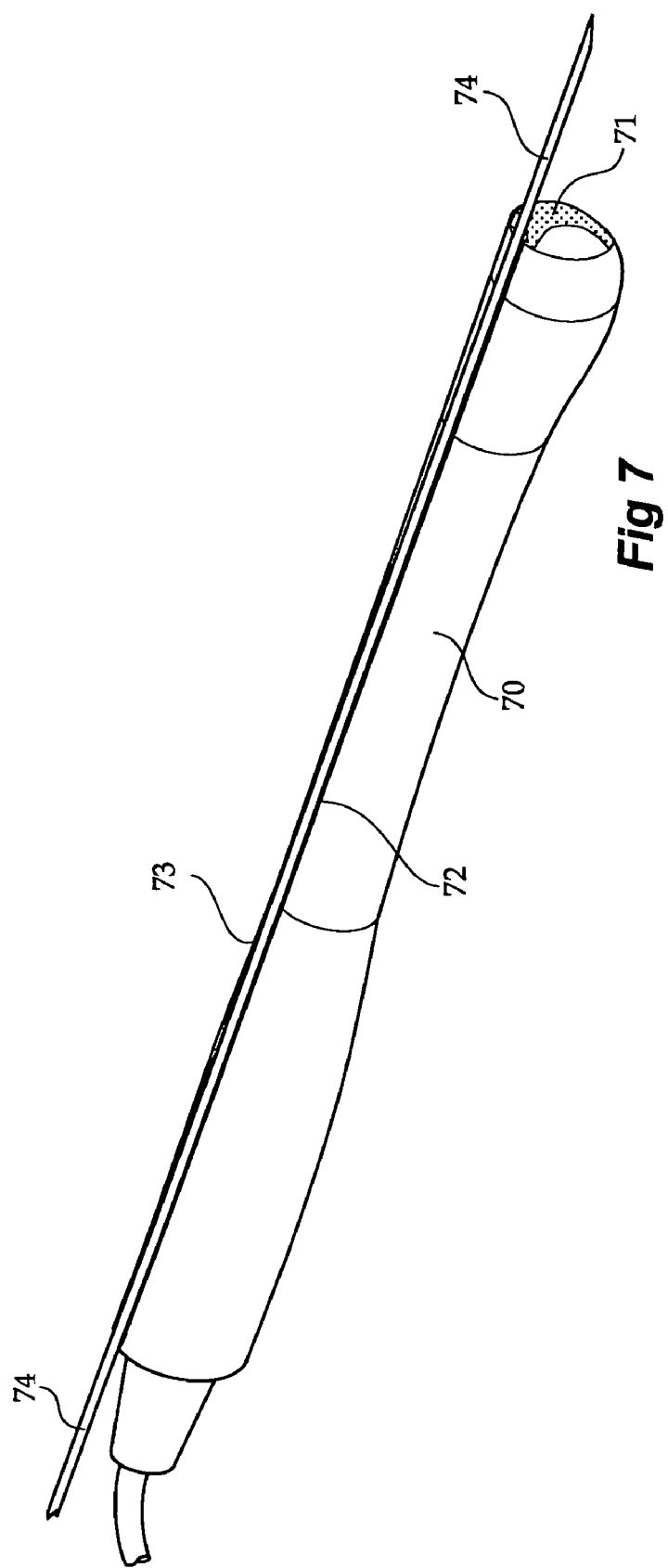

HEATED OVUM PICK UP NEEDLE

CROSS-REFERENCE TO RELATED APPLICATIONS

This application claims priority of provisional application Ser. No. 60/527,250, filed Dec. 5, 2003.

TECHNICAL FIELD

This invention relates to an aspiration and flushing needle arrangement adapted for the removal of oocytes from a female patient.

BACKGROUND OF THE INVENTION

During an oocyte retrieval procedure, a relatively long aspiration cannula may be inserted into a patient so that the distal end of the cannula is in contact with a patient's ovary. The objective is to puncture an individual follicle in the ovary and withdraw oocytes through the aspiration cannula. Generally the proximal end of the cannula is connected to flexible tubing, which is in turn connected to both a test tube and via the test tube to a vacuum source. The vacuum source provides suction via the test tube to the cannula to allow aspiration of the oocyte from the follicle. In some medical procedures to retrieve oocytes, the physician may puncture several follicles in turn to abstract oocytes from each without removal of the aspiration cannula from the patient.

Several different cannula styles are currently used for oocyte retrieval. One style is a single lumen device. This style requires that any irrigation to assist with the removal of an oocyte be conducted through the same fluid path or lumen that is used for aspiration. In such instances if an oocyte is lodged in the fluid path of the cannula the oocyte may be actually flushed back into the follicle during the irrigation procedure. Therefore the use of a single lumen may create the potential of losing the oocyte during the irrigation procedure. Accordingly, some physicians prefer the use of a dual lumen device for oocyte collection procedures. A dual lumen device has a first fluid path or lumen for aspiration and a second fluid path for irrigation or flushing. The use of separate paths thereby reduces the possibility of flushing an oocyte out of the aspiration path during an irrigation or flushing procedure.

Each oocyte is located in a fluid filled cyst or follicle. Before an oocyte can be retrieved, a physician needs to be able to accurately puncture each cyst prior to retrieval without damaging or losing the oocyte. In order to cleanly puncture the cyst, oocyte collection devices include a cannula having a sharpened bevelled tip. Ideally, the tip is gently inserted into the follicle to puncture the cyst and allow aspiration of the follicular contents. This releases the oocytes. This procedure can take some time, at least several minutes, for instance. During this period the needle or cannula could contain part or all of the follicular contents potentially containing one or more oocytes.

Studies have shown that irreparable damage can occur to an oocyte and particularly its meiotic spindle (or metaphase plate) when subjected to temperatures as little as 4° C. below the ideal of 37° C. This can result in fertilised oocytes having reduced viability even though there is no visible spindle damage. Higher temperatures may also damage an oocyte. Flushing medium held in the relatively long aspiration cannula can cool to an unacceptable degree while a physician is locating and puncturing a follicle and this cooler medium may cause damage to the oocyte.

To assist with insertion of the aspiration cannula an ultrasonic probe may be used. Where the oocyte recovery is done transvaginally a transvaginal ultrasonic probe may be used. The transvaginal ultrasonic probe has a needle guide associated with it and is used to support and aim the needle towards a follicle of an ovary after the transvaginal ultrasonic probe has been inserted into the vagina. The physician then advances the needle through the wall of the vagina into the ovary.

It is the object of this invention to provide a solution to this problem or to at least provide a physician with a useful alternative.

Throughout this specification the term distal is used to indicate that portion of the apparatus, that in use, is further away from the physician and the term proximal is used to indicate that portion of the apparatus, that in use, is nearer to the physician.

SUMMARY OF THE INVENTION

In one form therefore, although this may not necessarily be the only or broadest form, the invention is said to reside in an oocyte retrieval device including an aspiration needle, the oocyte retrieval device including an arrangement to maintain at least a part of the aspiration needle at or near a selected temperature.

The arrangement to maintain at least part of the needle at a selected temperature may be associated with the needle itself or it may be associated with a guide for the needle.

The guide for the needle may be mounted on or be part of an ultrasonic probe such as a transvaginal ultrasonic probe.

Preferably the selected temperature is just at or above or below the optimum temperature to maintain the oocyte during the collection procedure. More particularly the selected temperature is within plus or minus 4° C. of the body temperature, such as 37° C. for humans. Hence, the selected temperature is preferably in the range of from 33° C. to 41° C. and more preferably in the range of from 35° C. to 40° C. so that damage to an oocyte does not occur during retrieval.

The aspiration needle may be a single lumen needle, a dual lumen needle or a dual coaxial lumen needle.

The needle may be manufactured from a polymeric material, a metal such as stainless steel, ceramic or glass.

The arrangement to maintain at least part of the needle at a selected temperature may include means to maintain the temperature of the needle or to provide heating to the needle.

To maintain the needle or part of the needle at the selected temperature the needle may be manufactured from a high heat capacity or insulative material or the needle may have an insulative coating on it. Before use, the needle can be warmed to the selected temperature and then the insulative coating or material will assist in maintaining that temperature.

Arrangements to heat the needle may include one or more of the following.

A first method of heating the needle may be by providing a continuous flow of warmed media or saline through the needle before the oocyte retrieval step. For this arrangement the needle is preferably a dual lumen needle. In the dual lumen needle the lumens may be side by side or coaxial. Warmed media or saline can be supplied towards the tip of the needle in one of the lumens and returned through the other of the lumens. For coaxial lumens it may be preferable to supply the warmed media or saline through the outer lumen and to withdraw it through the inner lumen. Such a needle may include means to change from a recirculating or warming mode to an aspiration mode when a suitable oocyte has been selected. The means to change to an aspiration mode may be a two position tap on an aspiration tube with flow going to a waste receptacle until the tap is turned to the aspiration position at which time an oocyte may be aspirated to an a collection receptacle. The means to change to an aspiration mode such as a two position tap may include a construction which, when in the aspiration mode provides a minimum interruption to the flow of aspiration medium and hence reduce the potential of damage to the oocyte.

Alternatively there may be electrical means provided to heat the needle or at least keep the needle warm during its use.

Heating may be provided by a resistive heating wire, which is placed either inside or outside the lumen or embedded into the wall of the needle. Suitable insulation for the heating wire may be provided where necessary. Alternatively inductive heating of the needle may be provided by electromagnetic means where the needle is formed from a suitable metal.

Alternatively there may be provided a resistive layer or coating on the outside of the needle which when an electric current is passed through the resistive layer provides a resistive heating effect.

Suitable electronic controls may be provided in the handle of the ovum collection device or other suitable place to control the electrical, resistive or inductive heating. Such control arrangements may include feedback control to observe the temperature of the needle and adjust the degree of heating accordingly.

Where the arrangement to maintain at least part of the needle at a selected temperature is associated with the guide for the needle the guide may be supplied with, for instance, an electrical resistance heating pad to support and guide the needle. Other forms of heating may also be used such as recirculating fluids or the like.

In an alternative arrangement the invention may be said to reside in an ovum collection device including a handle, a collection needle extending from the handle, the collection needle having a sharpened tip for insertion into a follicle of an ovary, a collection duct in fluid communication with the collection needle and extending from the handle to a collection bottle and a heating arrangement to maintain the collection needle at a selected temperature.

The heating arrangement may be any one of the options discussed above.

In a further form, the invention is said to reside in an aspiration and flushing needle assembly having separable flushing and aspiration assemblies, the flushing assembly having a flushing needle connectable to a source of flushing liquid and the aspiration assembly having an aspiration needle connectable to an aspiration arrangement, the flushing and aspiration needle assemblies being connectable for use with the aspiration needle extending coaxially within the flushing needle to a distal end thereof and a heating arrangement to maintain at least part of the assembly at a selected temperature.

Once again, the heating arrangement may be any of the options discussed above and suitable electronic controls may be provided in a handle or other portion of the ovum collection or retrieval device to control the heating arrangement. Such control arrangements may include feedback control to observe the temperature of the needle and adjust the degree of heating accordingly.

In a further form the invention comprises a transvaginal ultrasonic probe comprising an elongate body, an ultrasonic transmitter and receiver arrangement at a distal end thereof, a groove extending along the elongate body, the groove being adapted to receive in use an aspiration needle for oocyte recovery, the groove including heating means adapted to maintain an aspiration needle when received in the groove at a selected temperature.

The heating means in the groove may be in the form of an electrical resistance heating pad to also support and guide the needle.

Preferably the selected temperature is just at or above or below the optimum temperature to maintain the oocyte during a collection procedure, wherein the temperature is 37° C. plus or minus 4° C.

BRIEF DESCRIPTION OF THE DRAWING

This then generally describes the invention but to assist with understanding reference will now be made to the accompanying drawings which show preferred embodiments of the invention.

In the Drawings:

FIGS. 4A and 4B show a dual lumen needle with continuous flushing of warmed media to provide heating in an alternative embodiment of an oocyte retrieval device;

FIGS. 5A and 5B show the use of a heating element on the outside of a single lumen needle in an alternative embodiment of an oocyte retrieval device;

FIGS. 6A and 6B show the use of a heating element in the lumen between an inner and outer lumens of a coaxial needle; and FIG. 7 shows an alternative embodiment of oocyte retrieval device associated with a transvaginal ultrasonic probe.

DETAILED DESCRIPTION

Figure 1:
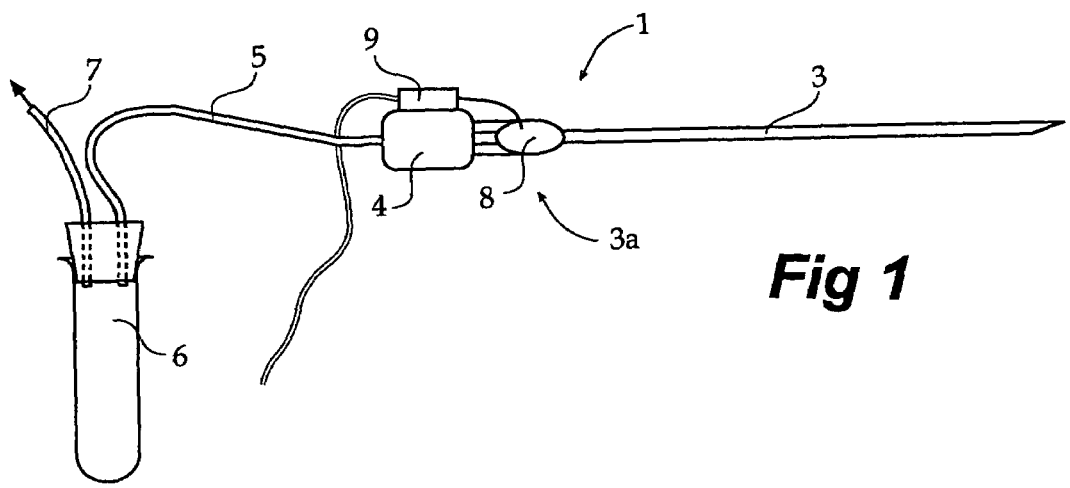
FIG. 1 shows a first embodiment of heated oocyte retrieval device according to the invention incorporating electromagnetic induction heating of the needle.

Now looking more closely at the drawings and in particular the embodiment shown in FIG. 1. In this drawing it will be seen that the ovum collection device 1 of this embodiment has a needle 3 extending from a handle 4. A tube 5 which is in fluid communication with the needle 3 through the handle 4 extends to a collection bottle 6 from which an aspiration line 7 extends. An inductive heating device shown schematically as 8 is mounted onto the proximal end 3a of the needle 3 and is controlled by electrical controller shown schematically as 9. The electromagnetic inductive heating device 8 may include a coil extending along at least a part of the needle inside, in or outside the wall of the needle. The electromagnetic inductive heating device 8 maintains the needle and hence the media within it at a temperature preferably in the range of from 33° C. to 41° C. and more preferably in the range of from 35° C. to 40° C. so that damage to an oocyte does not occur during retrieval.

Figure 2:
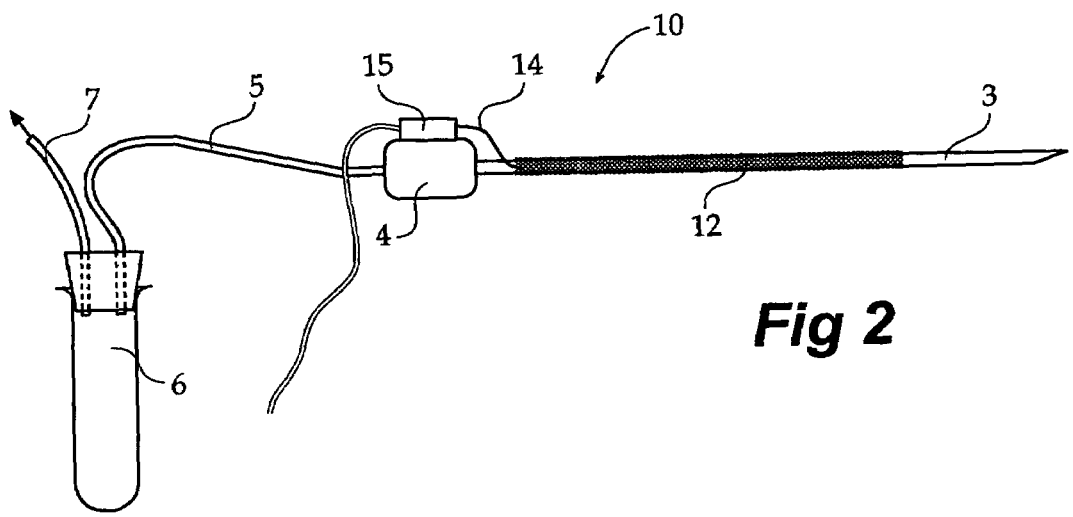
FIG. 2 shows an alternative embodiment of oocyte retrieval device including a resistive surface coating on the needle to act as a resistive heating element.

In the embodiment shown in FIG. 2, a similar construction of ovum collection device 10 is shown and the same reference numerals are used for the same components. The ovum collection device 1 of this embodiment has a needle 3 extending from a handle 4. A tube 5 which is in fluid communication with the needle 3 through the handle 4 extends to a collection bottle 6 from which an aspiration line 7 extends. In this embodiment, however, an outer surface coating 12 of a resistive material is provided on at least a portion of the needle and when a current is provided, by means of wire 14 from a controller 15 mounted onto the handle 4, resistive heating of the needle may be obtained to maintain the needle at the selected temperature. Suitable thermal and electrical insulation may be provided over the surface coating of resistive material.

Figure 3A:
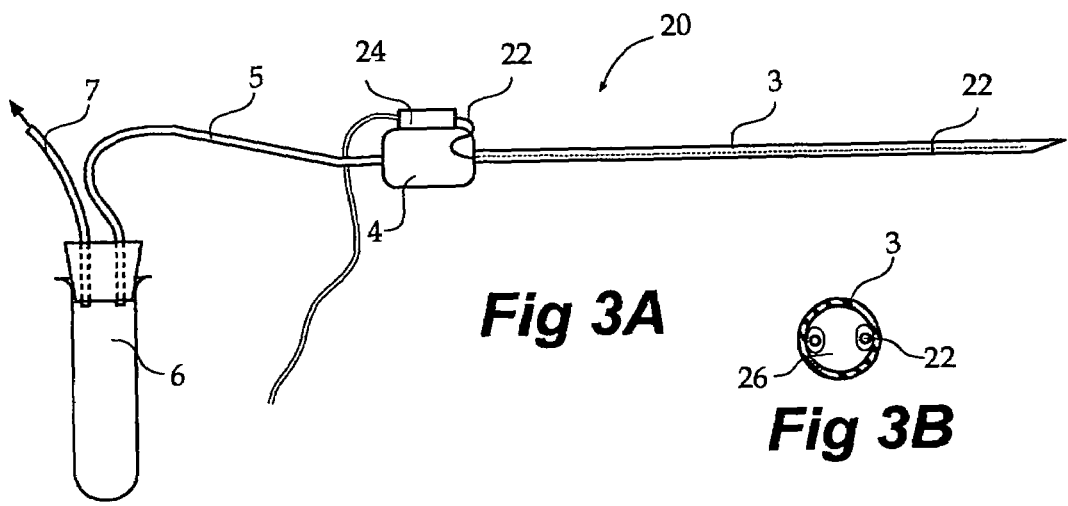
FIGS. 3A and 3B show the use of a heating wire within the lumen of a cannula or needle in an alternative embodiment of an oocyte retrieval device.
Figure 3B:
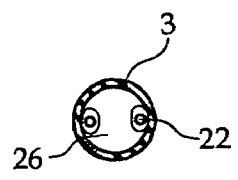

FIGS. 3A and 3B show a similar needle arrangement for an ovum collection device 20. FIG. 3B shows a cross section of the needle. The same reference numerals are used for the same components as in FIG. 1. The ovum collection device 1 of this embodiment has a needle 3 extending from a handle 4. A tube 5 which is in fluid communication with the needle 3 through the handle 4 extends to a collection bottle 6 from which an aspiration line 7 extends. In this embodiment, there is provided a continuous insulated electrical heating wire 22 extending within and along at least a portion of the needle 3 from an electrical controller 24 mounted onto the handle 4. By this arrangement, an electrical heating may be provided from the wire 22 to maintain media within the lumen 26 of the needle 3 at a selected temperature. The wire may be in a spiral form within the needle to ensure good contact between media and heating wire 22.

FIGS. 4A and 4B show an alternative embodiment of ovum collection device. FIG. 4A shows a general view of the device and FIG. 4B shows a cross section of the needle assembly. The ovum collection device 30 has an outer needle 31, an inner needle 36 and an annular lumen 45 between the inner and outer needles. In this embodiment the outer needle 31 extends from a handle 32. Within the handle 32 is a lumen 33 and the annular lumen 45 of the needle 31 is in fluid communication with the lumen 33. A duct 34 from a media source 35 is also in fluid communication with the lumen 33 and hence the annular lumen 45 of the needle 31. Within the outer needle 31 is the inner needle 36 which is coaxial with the needle 31 and which passes through without opening into the lumen 33 in the handle 32 and extends out at the rear of the handle 32. At the rear of the handle 32 there is a tap 37 which is selectable to either direct flow from the inner needle 36 via duct 38 to a waste receptacle 39 or via a collection tube 40 to a collection bottle 41. The collection bottle 41 has an aspiration tube 42 and the waste bottle 39 also has an aspiration tube 43. The inner needle 36 extends towards the end of the outer needle 31 but is terminated shortly before the tip 44 of the outer needle 31.

Optionally, the duct 34 from the media source 35, the collection tube 40 to the collection bottle 41 and the aspiration tube 42 are insulated to prevent heat loss or they may have some form of heating such as a heating sleeve or a heating resistance wire extending through the tubes.

In use, the aspiration tube 43 is used to draw warmed media which is maintained at or about the selected temperature from the source 35 through the duct 34 and hence into the outer lumen of the needle 31. Once the needle has punctured the body of the patient the tip is "closed off" and media can be drawn to the tip in the outer lumen and from this lumen the warmed fluid is drawn into the inner needle 36 and via tap 37 to waste 39. Alternatively, to ensure recirculating flow, there may be an arrangement to close off the tip of the dual lumen needle until aspiration is required.

This flushing can be done continuously but at a low flow rate until such time as a follicle has been successfully punctured or is just about to be punctured at which time the tap 37 can be operated to cause aspiration in the inner needle 36 to occur from the tube 42 via the collection bottle 41 and the tube 40 so that an ovum is drawn through the needle 36 via the tap 37 to the duct 40 and into the collection bottle 41. Alternatively, by using a vacuum rate greater than the flushing rate continual cycling of warm fluid through the needle may be obtained.

The tap 37 is preferably of a type which, when in the position to allow flow from the needle 36 to the tube 40, provides little or no obstruction to flow so as not to damage an oocyte passing through it.

FIGS. 5A and 5B shown an alternative arrangement of needle heating arrangement. FIG. 5A shows a general view of the device and FIG. 5B shows a cross section of the needle. An ovum pick up needle 50 has an insulated wire 51 on the outside of the needle 52 and is controlled by a controller 53. Once again electrically resistive heating of the wire can cause the media within the needle to be kept at a selected temperature.

FIGS. 6A and 6B show a further embodiment of a dual coaxial lumen needle heating arrangement. FIG. 6B shows a cross section of the needle. The ovum collection device 60 of this embodiment has a needle assembly comprising an outer needle 62, an inner needle 61 and an annular lumen 66 between the inner and outer needles. The needle assembly extends from a handle 65. A tube 5 which is in fluid communication with the inner needle 61 through the handle 65 extends to a collection bottle 6 from which an aspiration line 7 extends. In this embodiment a heating wire 63 with suitable insulation is directed in the lumen 66 between an inner needle 61 and an outer needle 62 of the ovum collection device 60. Once again electrical control through a controller 64 mounted onto the handle 65 can be provided to maintain the needle at the selected temperature. Once again, the wire 63 may be in a spiral form in the lumen 66 between the inner and outer needles to provide good contact between the heating wire and the media.

FIG. 7 shows a transvaginal ultrasonic probe 70 which is used to obtain high resolution image of the ovaries. By the transvaginal route ovaries are only several centimeters from the probe tip 71. A needle guide 72 is attached to or provided in the upper surface of the transvaginal ultrasonic probe. In this embodiment the needle guide is a groove along the length of the transvaginal probe. An aspiration needle 74 is placed into the needle guide and the aspiration needle 74 can be moved longitudinally within the guide 72. The guide 72 in this embodiment includes a resistance heating element 73 with suitable controllers (not shown) to maintain the aspiration needle 74 at the selected temperature. The guide and resistance heating element can be integral with the transvaginal ultrasonic probe but alternatively they are a single unit which can be mounted onto a range of probe models. The guide may be reusable or disposable.

It will be appreciated by those skilled in the art, that the invention is not restricted in its use to the particular application described and neither is the present invention restricted in its preferred embodiment with regard to the particular elements and/or features described or depicted herein. It will be appreciated that various modifications can be made without departing from the principles of the invention, therefore, the invention should be understood to include all such modifications within its scope as defined by the claims.

What is claimed is:

1. A transvaginal ultrasonic probe comprising an elongate body, an ultrasonic transmitter and receiver arrangement at a distal end thereof, a groove extending along the elongate body, the groove being adapted to receive in use an aspiration needle for oocyte recovery, the groove including heating means adapted to maintain an aspiration needle when received in the groove at a selected temperature.

2. A transvaginal ultrasonic probe as in claim 1 wherein the selected temperature is 37° C. plus or minus 4° C. being just at or above or below the optimum temperature to maintain the oocyte during a collection procedure.

3. A transvaginal ultrasonic probe as in claim 1 wherein the heating means in the groove comprises an electrical resistance heating pad which also supports and guides the needle.

4. A transvaginal ultrasonic probe in combination with an aspiration needle, the transvaginal ultrasonic probe comprising an elongate body, an ultrasonic transmitter and receiver arrangement at a distal end thereof, a groove extending along the elongate body, the groove receiving in use the aspiration needle for oocyte recovery, the groove including heating means adapted to maintain the aspiration needle when received in the groove at a selected temperature.

5. A transvaginal ultrasonic probe in combination with an aspiration needle as in claim 4 wherein the aspiration needle is selected from a group comprising a single lumen needle, a dual lumen needle or a dual coaxial lumen needle.

6. A transvaginal ultrasonic probe in combination with an aspiration needle as in claim 4 wherein the aspiration needle is manufactured from a material selected from polymeric material, a metal, a ceramic or a glass.

7. A transvaginal ultrasonic probe in combination with an aspiration needle as in claim 4 wherein the selected temperature is 37° C. plus or minus 4° C. being just at or above or below the optimum temperature to maintain the oocyte during a collection procedure.

8. A transvaginal ultrasonic probe in combination with an aspiration needle as in claim 4 wherein the heating means in the groove comprises an electrical resistance heating pad which also supports and guides the needle.

* * * * *